(12) United States Patent
Van Der Heijden et al.

(10) Patent No.: US 8,562,597 B2
(45) Date of Patent: Oct. 22, 2013

(54) DEVICE, ASSEMBLY AND METHOD FOR COLD TREATING A TISSUE

(75) Inventors: Henricus Maria Van Der Heijden, Oldeholtpade (NL); Govardus Dirk Johannes Titus Maria Van Nunen, Apeldoorn (NL)

(73) Assignee: Koninklijke Utermöhlen N.V., Wolvega (NL)

( * ) Notice: Subject to any disclaimer, the term of this patent is extended or adjusted under 35 U.S.C. 154(b) by 881 days.

(21) Appl. No.: 12/301,628

(22) PCT Filed: May 16, 2007

(86) PCT No.: PCT/NL2007/050225
§ 371 (c)(1),
(2), (4) Date: Mar. 2, 2009

(87) PCT Pub. No.: WO2007/139378
PCT Pub. Date: Dec. 6, 2007

(65) Prior Publication Data
US 2009/0209952 A1 Aug. 20, 2009

(30) Foreign Application Priority Data

May 25, 2006 (NL) .................................. 1031888

(51) Int. Cl.
*A61B 18/02* (2006.01)
*B65D 83/00* (2006.01)

(52) U.S. Cl.
USPC ............................. 606/25; 606/23; 222/402.1

(58) Field of Classification Search
USPC ....................... 606/20–26; 222/402.1–402.13
See application file for complete search history.

(56) References Cited

U.S. PATENT DOCUMENTS

| | | | |
|---|---|---|---|
| 3,739,941 A * | 6/1973 | Ostrwosky et al. | 222/153.11 |
| 3,823,427 A * | 7/1974 | Pittet | 4/255.01 |
| 3,946,911 A * | 3/1976 | Morane et al. | 222/402.11 |
| 5,649,530 A * | 7/1997 | Ballini | 128/200.14 |
| 5,945,111 A * | 8/1999 | Esser | 424/401 |
| 6,226,996 B1 | 5/2001 | Weber et al. | |
| 6,296,410 B1 * | 10/2001 | Ruizendaal | 401/119 |
| 7,604,632 B2 * | 10/2009 | Howlett et al. | 606/25 |
| 7,819,288 B2 * | 10/2010 | Healy et al. | 222/162 |
| 2004/0188473 A1* | 9/2004 | Groh et al. | 222/402.13 |
| 2005/0043723 A1 | 2/2005 | Howlett et al. | |

FOREIGN PATENT DOCUMENTS

| | | |
|---|---|---|
| EP | 1586277 A1 | 10/2005 |
| GB | 2 244 922 | 12/1991 |
| WO | WO00/10889 | 3/2000 |
| WO | WO 2006/004407 | 1/2006 |

* cited by examiner

*Primary Examiner* — Matthew F DeSanto
(74) *Attorney, Agent, or Firm* — Hoffmann & Baron, LLP

(57) ABSTRACT

The invention relates to a device for cold treating a tissue. The invention also relates to an assembly of such a device and a container comprising a cryogenic liquid, such as a spray can. The invention further relates to a method for cold treating a tissue.

25 Claims, 4 Drawing Sheets

DEVICE, ASSEMBLY AND METHOD FOR COLD TREATING A TISSUE

This application is the U.S. National Phase of, and Applicants claim priority from, International Application Number PCT/NL2007/050225 filed May 16, 2007 and Netherlands Patent Application No. 1031888 filed May 25, 2006 which are incorporated herein by reference.

BACKGROUND OF THE INVENTION

1. Field of the Invention

The invention relates to a device for cold treating a tissue. The invention also relates to an assembly of such a device and a container comprising a cryogenic liquid, such as a spray can. The invention further relates to a method for cold treating a tissue.

2. Background of the Invention

There are different forms of cold treating a tissue. Some of them are aimed at cooling the tissue to a temperature that is above 0 degrees Centigrade. In that case, no damage is caused to the tissue. Other forms are aimed at freezing the tissue, such that under the tissue a blister forms which ensures that the tissue disappears in time. Because this involves purposive damaging of tissue, care is to be devoted to the safety of the treatment.

Freezing of tissue, especially warts, is usually realized by the use of an applicator, which applicator can take up cryogenic liquid and deliver the cryogenic liquid, or the cold generated by evaporation of the cryogenic liquid, to the tissue to be cooled. British patent publication GB2244922 describes an applicator of stainless steel with a hollow space, which can be dipped in liquid nitrogen so that the tip is cooled. The cold applicator tip is thereupon brought into contact with the tissue to be cooled. Another known form of such an applicator is a cotton bud. It absorbs the liquid nitrogen and is then held against the tissue to be cooled. Here, the liquid nitrogen comes into direct contact with the tissue and consequently the procedure should only be performed by an expert. In newer forms that are commercially available and can be performed by anyone, the applicator comprises foam plastic material which can take up cryogenic liquid from a spray can and deliver the cold released upon evaporation of this cryogenic liquid to the tissue to be cooled. Such porous applicators are known for instance from US200510043723 and WO2006/004407. The cryogenic liquid is then chiefly used for cooling the applicator, which applicator thereupon cools the tissue to be cooled. In this way, the cryogenic liquid is not utilized optimally. Moreover, the cold from the applicator in most cases does not come into contact with the entire tissue to be cooled. If the tissue is for instance a wart and the wart forms a protrusion on the skin, then, with this applicator, in practice only the upper side of the tissue is frozen. As a consequence, a frequently occurring problem in treating warts with such an applicator is that only the upper side of the wart disappears and the wart grows again later. A preformed applicator would be too specific for a single shape of a wart and cannot ensure direct contact with a capriciously or aberrantly shaped wart. With a better deformable applicator a part of the tissue surrounding the tissue to be cooled may be wrongly damaged. Yet another disadvantage is that the applicator, with the cryogenic liquid included in it, is not screened from the environment during use, that is, upon movement of the applicator from the container with cryogenic liquid to the tissue to be cooled, so that by accident another part of the skin may be touched, resulting in unwanted damage. In addition, the applicator needs to be saturated with cryogenic liquid for an optimum result, which entails the possibility of drops of cryogenic liquid falling off. A still further disadvantage is that the cold treatment with an applicator is less well reproducible. The force with which the applicator can be pressed against the tissue and the time between the taking up of the cryogenic liquid by the applicator and the application of the applicator to the tissue to be cooled are variable. The foam plastic applicator is marketed together with a spray can to provide the applicator with cryogenic liquid. This spray can comprises a valve which is not dosable. Such a valve, however, entails a considerable chance of hazardous situations because the valve, when improperly used, may be kept depressed continuously, allowing cryogenic liquid thereby released to damage other tissue. Since the valve does not allow of dosing, the amount of cryogenic liquid released is highly variable, which renders the use less reproducible. Typically, to ensure saturation, too much cryogenic liquid will be used.

Freezing a tissue can also be realized by spraying the cryogenic liquid directly onto the tissue to be cooled. This is known, for instance, from WO2005/011560 and EP1586277. In that case, to prevent unwanted damage, the other ambient tissue may be covered or a collar is placed around the tissue to be cooled. The device of WO2005/011560, for instance, can be provided with an end-piece to maintain a minimum distance between spray opening and tissue to be treated. Even so, the risk of improper use and of undesirable damage is so high that this method is therefore to be performed only by an expert. Another important disadvantage of the methods whereby the cryogenic liquid is sprayed directly onto the tissue is that although the surface of the tissue to be cooled cools down rapidly, this effect is rapidly gone again because the cryogenic liquid evaporates rapidly. The cold does not get a chance to penetrate deeply into the tissue. This method is moreover poorly reproducible because the distance from the spraying device to the tissue to be cooled is typically variable and also the ambient temperature and air humidity have a strong influence on the cooling action.

Accordingly, there is a need for a device and a method for reproducibly cold treating a tissue, in particular a wart, which is safe in use and by which the tissue to be cooled is cooled down or frozen deeply into the core. There is also a need for a safe assembly for practicing the cold treatment, which assembly preferably comprises a dosing valve. The object of the present invention is to provide such a solution.

SUMMARY OF THE INVENTION

The invention to that end provides a device for cold treating a tissue, which device comprises a chamber, which chamber comprises a first opening ('inlet opening') for letting cryogenic liquid into the chamber. The chamber comprises a second opening ('delivery opening') for delivering the cold to the tissue to be cooled. The cold in the chamber is thus in direct contact with the tissue to be cooled and can thus cool off the tissue to be cooled, deeply into the core. The advantage of such a device, also called application cap, is that the cold that is generated by evaporation of the cryogenic liquid can be retained for a period of time in the chamber screened from the environment by a wall, and for that period of time can be delivered to a tissue that needs to be cooled or frozen deeply into the core thereof. This is especially of relevance in removing a wart by means of cold (cryotherapy), whereby the whole wart, that is, including the core of the wart, is to be frozen. In fact, only then is a blister formed under the wart, which blister ensures that the wart will disappear. By retaining the cold in the chamber, moreover, the amount of cryogenic liquid is utilized considerably more efficiently than with a foam plastic applicator. The efficiency of the cryogenic liquid also enables the use of a readily obtainable commercial dosing valve. As the cold, in the use thereof, remains mainly in the chamber and on the tissue to be cooled, such an application cap is moreover safe in use. For that reason, it may be used by anyone. The wall of the chamber is preferably insulating, so that less cold is dissipated to the environment. Consequently, the cryogenic liquid can be utilized more efficiently and the application cap is still safer in use.

The device of the present invention hence differs from the device as described in WO2006/114532, which is part of the fictional prior art, in that the chamber according to the invention converges in the direction of the delivery opening and further that the chamber is screened from the environment by a wall. The wall of the protective cap of WO2006/114532, by contrast, includes a number of openings of relatively large dimension. The cap of WO2006/114532 is therefore unsuited for retaining cold and moreover entails the hazard of the cryogenic liquid introduced into the chamber coming undesirably into contact with the environment. Like the end-piece in WO2005/011560, the cap of WO2006/115643 serves for creating a minimum distance between spray opening and the surface to be cold treated.

The volume of the chamber according to the invention is preferably at least 1 cm$^3$, such as between 1 and 100 cm$^3$, preferably between 1 and 20 cm$^3$. The volume of the chamber is preferably large enough to enable evaporation but small enough to keep the cold concentrated. This volume is related to the volume of the tissue that is to be cooled. Further, the most favorable volume depends on the amount of cryogenic liquid that is driven through the first opening, the size of the liquid particles, the rate and direction with which the liquid particles are driven through the first opening, and the like. When the term "cold" is used, this means a temperature that is lower than the temperature of the tissue. This may be a temperature between 0 and 25° C. as well as a temperature far below 0° C., such as −20° C. or lower. The device is therefore also applicable for freezing a tissue to a temperature that is far below 0° C.

The ratio between the volume of liquid gas and the volume of the chamber is preferably such that the gas can be introduced, the air at that moment disappears from the chamber, the gas is led to the second opening, so that evaporation occurs on the tissue and surroundings with a time span and temperature that meet the desired result. By properly tuning these conditions to each other, it is possible to realize this with only a slight amount of cryogenic liquid.

If the tissue to be cooled is a wart and the wart forms a protrusion on the skin, the second opening is preferably so large that the tissue to be cooled can be received in it with a proper fit. This provides the major advantage that the tissue is cooled from multiple sides, hence also laterally, thus allowing the cold to penetrate deeply into the core and enabling blister formation under the tissue (wart). The second opening can also be used for direct spraying of the cryogenic liquid onto the tissue to be cooled. The chamber then serves additionally for retaining the cold that is released from the tissue upon evaporation of the cryogenic liquid. Preferably, during the cold treatment, the second opening is directed downwards because cold usually sinks and will thereby concentrate around the second opening. This position of the device is especially of relevance if a particular amount of cryogenic liquid is to end up on the tissue, which amount evaporates only after some time.

In an aspect of the invention, the second opening is closed off by a cold-conducting material, preferably a membrane. This is especially favorable if it is not desirable, and moreover not necessary, for the cryogenic liquid to end up directly on the tissue to be cooled. The pain sensation in the use of such a device will be much less.

When further in the invention "second opening" is mentioned, this is understood to encompass a second opening that is closed by a cold-conducting material, preferably a membrane.

In an embodiment of the device according to the invention, a first part of the chamber, in which first part the second opening is present, converges in the direction of the second opening. Such a shape is especially favorable because the cold thus concentrates around the second opening, so that the cold intensifies there and hence the tissue to be cooled cools off more rapidly and the cold penetrates more deeply into the tissue. The invention therefore provides an application cap for cold treating a surface, which application cap comprises a chamber screened from the environment by a wall, which chamber comprises a first opening for letting cryogenic liquid into the chamber and comprises a second opening for delivering the cold to the surface to be cooled, such as tissue, while a first part of the chamber, in which first part the second opening is present, converges in the direction of the second opening.

The first part of the chamber is preferably essentially semicircular and essentially concentric with the second opening. In a specific embodiment, the chamber has substantially the shape of an elliptic paraboloid (see FIG. 1). This is the most favorable shape of the chamber because, as soon as the second opening is placed over the tissue to be treated, around the second opening a temperature gradient is created whose center will be in the proximity of the second opening and will attain the lowest temperature for the longest period of time. As cold usually sinks, the coldest point in the chamber will likewise sink and, when the chamber is held in a position in which the second opening faces down, be still more in the proximity of the second opening. The spherical sphere obtained by the elliptic paraboloid shape of the chamber will ensure that the coldest point remains as cold as possible without whirls and/or unnecessary warming due to an unnecessarily large surface.

It is preferred that the first opening and the second opening are essentially coaxial. Such a device makes it possible for a part, preferably the most part, of the cryogenic liquid that is driven through the first opening to end up on the tissue to be cooled. When the second opening is directed downwards, such a device is especially favorable because the liquid and the cold generated thereby are jointly driven to the second opening and hence to the tissue, which cools off more rapidly as a result. To avoid whirls of cold gas mixtures in the chamber, preferably both the first opening, the second opening and the chamber are essentially coaxial and the chamber has a streamlined shape which leads the flow of the mist and the cold to the second opening, preferably in a chamber which essentially converges in the direction of the second opening, is further essentially semicircular, and is essentially concentric with the second opening.

In another embodiment of a device according to the invention, a second part of the chamber, which second part adjoins the side of the first part facing away from the second opening, is essentially cylindrical, the second part and the second opening are essentially coaxial, and the first diameter of the second part is 2 to 4 times greater than the second diameter of the second opening. If the second opening is directed downwards, this shape is most optimal to enable evaporation, to keep the cold as concentrated as possible and to lead the cryogenic liquid and the cold to the second opening without unnecessary whirls and without unnecessarily large surface.

It is particularly favorable if the first opening is a passage in a spray piece, which spray piece comprises a channel for allowing the cryogenic liquid to pass out of the spray can, while the channel and the passage are in line with each other and are directed towards the second opening. Such a spray piece is especially useful for leading the cryogenic liquid in the direction of the second opening. Preferably, the most part of the cryogenic liquid ends up on the tissue to be cooled. This results in rapid initial cooling off. After that, the cryogenic liquid can evaporate from the tissue again and the cold thereby generated remains in the chamber around the tissue. Compared with direct spraying onto the tissue to be cooled in the cryogenic therapy according to the prior art, with this device the distance to the tissue to be cooled is defined by the dimension of the chamber; the ambient temperature and air humidity are less of influence on the result because in the use of the present device the environment around the tissue to be cooled is bounded by the wall of the chamber; the nozzle, owing to the shape and the volume of the chamber, can be geared to the cooling, preferably freezing, of a specific tissue, and the treatment is easier to perform on sites which, especially with children, are difficult to access, as between the legs or between the fingers. Warts are often found on these sites.

In an embodiment, a device according to the invention comprises at least one third opening to prevent overpressure upon spraying cryogenic liquid into the chamber. Preferably, the at least one third opening, also called vent hole, is situated in the vicinity of or immediately adjacent to the inlet opening and facing away from the second opening in order to prevent contact of the cryogenic liquid with unwanted surface or environment. Also, with a view to loss of cryogenic liquid through one or more vent holes, the latter are preferably situated away from the spray direction. In case the first part of the chamber has an elliptic paraboloid shape, then, during the introduction of the cryogenic liquid into the chamber, the air present in the chamber will be pushed away via the vent hole facing away from the second opening. Because the cryogenic liquid is heavier than air, it will remain concentrated in the lowermost portion of the chamber (i.e., the first part in which the second opening is situated). There, the cold will be generated and remain concentrated.

Apart from the first and second opening and any vent holes, the wall of the chamber is preferably closed completely. The wall can be made of any suitable material that on the one hand is resistant to the chemical composition of the cryogenic liquid and on the other hand can tolerate a low temperature without becoming fragile. Suitable materials are known to those skilled in the art, and comprise inter alia polymeric materials, such as polypropylene, polystyrene, polyester and the like. It is also possible to use a type of glass or a High Impact Polystyrene (HIPS).

It is important that the material does not unduly absorb the cold released by the cryogenic liquid. The cryogenic liquid would then evaporate too slowly and generate insufficient cold. On the other hand, the material must be sufficiently insulating to prevent the liquid evaporating too fast and the total duration of the cold treatment being too short. Preferably, a material is chosen whereby the cold in the chamber is maintained for at least 10 seconds. In addition, the wall thickness and/or the material properties of the material are preferably such that the environment is sufficiently protected from undesired cold by touching (convection cold) of the material.

Suitable materials have a relatively low heat conduction coefficient (lambda or $\lambda$; unit W/mK). The lower the $\lambda$-value, the more poorly the material conducts heat and hence the better it insulates. The material has for instance a heat conduction coefficient of 0.1-0.4 W/mK, preferably approximately 0.2 W/mK. The average specific mass (rho) of the material may also vary, but is typically between 700 and 1100 kg/m$^3$, preferably approximately 900 kg/m$^3$. This makes it possible to conduct the heat sufficiently without the heat being absorbed too much by the surrounding material.

The heat conduction coefficient is a constant value for any given material, regardless of the thickness of the material. The thickness of a wall of an application cap can vary and depends, for instance, on the material used. The heat resistance R of a particular thickness of a material is denoted in m$^2$K/W. Suitable materials have a heat resistance of approximately 1400-1500 m$^2$K/W.

In an embodiment, at least a part of the wall of the chamber includes a temperature indicator, so that it is possible to give the user an indication of the temperature of the chamber. The indicator may be provided (externally) on the wall and/or form an integral part of the material of the wall. The indicator is preferably a visually perceptible indicator, such as a temperature-sensitive pigment. Other suitable temperature indicators are based on liquid crystal display (LCD). By means of a change in the color of the application cap, it is possible to represent an indicative signal that the treatment or freezing of tissue has been achieved or completed.

This has been possible by impregnating the material with a pigment that is wholly incorporated in the plastic. According to desire, the color may for instance change, from 5° C., from white to blue. Depending on the point where the indicator is provided, the color change can denote that the application cap is cold and/or cold enough. Conversely, it may be determined via a color that the cap is not cold anymore, or cold enough.

A device according to the invention can include a first construction part, which first construction part comprises the second opening (the delivery opening) and is detachably connected with the remaining part of the device. Thus, different construction parts, whose diameter of the delivery opening varies, can be readily coupled to the device. In this way, tissues of different dimensions can be treated. The construction part can comprise the first part of the chamber. It is also possible that the construction part comprises both the first part and a part of, or the whole of, the second part.

The chamber preferably comprises a cylinder-shaped first collar, directed towards the outside of the chamber, which first collar surrounds the second opening. The first collar can keep the cryogenic liquid concentrated on the tissue to be cooled and thus better cool off the tissue to be cooled. In a preferred treatment which utilizes the device according to the invention, initially the collar is filled with cryogenic liquid so that the cryogenic liquid is present on the tissue for some time and then evaporates. The tissue can then initially adopt the temperature of the evaporation temperature of the cryogenic liquid. The first collar is also favorable for positioning the device relative to the tissue. Preferably, the inside diameter of the first collar is substantially equally large as the diameter of the second opening and the collar links up with the second opening in a form-closing manner. The inside diameter of the collar is preferably the same throughout. Owing to the collar, the user can see better where the second opening is placed on the tissue. Moreover, when the tissue to be cooled is a protrusion of the skin, such as a wart, the user can readily feel by way of the first collar whether the first collar surrounds the tissue to be cooled. The tissue to be cooled, for instance wart, can even be pushed into the chamber to some extent. The first collar may be translucent, allowing the user to properly see whether the device is properly positioned. The collar preferably surrounds the wart in such a way that the wart does not touch the collar because otherwise the cryogenic liquid could not properly reach all points around the wart. On the other hand, the tissue surrounding the wart should be damaged to the least possible extent or preferably not at all. The dimension of the collar is therefore important. It is advantageous if the first collar is detachably connected with the device because this allows different collars of different dimensions to be used. Also, replacing the collar can prevent reinfection.

The end of the first collar facing away from the chamber is preferably 1-5 mm wide, more preferably 2-3 mm, and lies in one plane. By virtue of a first collar with such an end, the surface of the device that is placed around the tissue to be cooled is larger, so that the forces around the tissue to be cooled are better distributed and the pressing of the end of the first collar around the tissue to be cooled is less inconvenient. The pressing of the end of the first collar around the tissue to be cooled is favorable because the tissue to be cooled then closes off the chamber and the tissue to be cooled is then optimally cooled.

Further, the chamber can comprise a second collar, directed towards the inside of the chamber, which second collar surrounds the second opening. Such a second collar is especially advantageous because it can stop an excess of non-evaporated cryogenic liquid. For this purpose, however, it is then important that the chamber be held such that the second opening is directed downwards. For this purpose, further, the end of the second collar should not touch the inner wall. The principle of the second collar is that the liquid that is driven against the wall of the chamber, which liquid has not evaporated yet, will collect between the wall of the chamber and the second collar. From that position, the treatment liquid can evaporate again in the proximity of the second opening, so that the tissue can be cooled off still more intensely. This process can be part of the cold treatment but can also serve only as a safety measure. If such a second collar is lacking, then, due to possible improper use, an excess of cryogenic liquid may end up on the tissue to be cooled, so that, after detaching the device from the tissue to be cooled, the excess liquid comes into contact with the surrounding tissue and causes unwanted damage.

In another aspect, the invention provides an assembly of a) a device for cold treating a tissue, and b) a container with cryogenic liquid, wherein the application cap comprises a chamber screened from the environment, which chamber comprises a first opening for letting cryogenic liquid into the chamber, and wherein the chamber comprises a second opening for delivering the cold to the tissue to be cooled, and wherein the outlet opening of the container is in communication with the first opening. Such an assembly is essentially sufficient for one or more cold treatments, that is, no extra elements, such as applicators, are needed for cold treatment. This assembly can be used by anyone. An assembly preferably comprises a device as described above (application cap). In a preferred embodiment, the container is a spray can with cryogenic liquid, wherein the valve of the spray can is in communication with the first opening. The valve in a preferred embodiment of the assembly according to the invention is a dosing valve, that is to say a valve having a filling chamber which valve upon actuation releases a defined amount of cryogenic liquid. Through the presence of a dosing valve, the risk of continuous and excessive release of cryogenic liquid, and hence of unwanted damage to the skin, is much lower. A dosing valve moreover enables more easily and better reproducible use of the assembly.

The container, such as a spray can, in the assembly preferably contains an amount of cryogenic liquid that has been measured for 2-4 cold treatments. Due to the limited content of the spray can, such an assembly is safer in use. It can also be implemented as a very small assembly, which is practical in the use thereof. As the device in the assembly deals efficiently with the cryogenic liquid, the spray can may be very small. But for the same reason the spray can may have the conventional size and contain just enough cryogenic liquid for multiple, for instance more than 100, cold treatments. The term 'cold treatment' as used herein usually concerns a cold treatment wherein the tissue is brought for a given time period, preferably at least 5 seconds, to a temperature of less than $-10°$ C.

Prior to use, the chamber is filled with air, i.e., the chamber is a hollow space and not provided with any absorbing material, such as a porous foam. This makes it possible to introduce a cryogenic liquid into the chamber several times without this space being subject to variation and/or change as would be the case if the space were filled with an absorbing material.

The container preferably contains a cryogenic liquid which has little or no impact on the environment, in particular a halogen-free cryogenic liquid. The liquid is preferably homogeneous and can serve as a solvent for supplementary therapeutic and/or cosmetic additives. It is for instance methane, propane, isobutane, n-butane, dimethyl ether, liquid nitrogen or liquid helium. Preferably, dimethyl ether or liquid nitrogen is used, more preferably dimethyl ether. Also, mixtures of two or more cryogenic liquids can be used, such as a mixture of dimethyl ether and propane.

In a particular aspect, the container contains a cryogenic liquid and, for instance dissolved therein, at least one additive which can be used in a directed manner and/or in cooperation with the cryogenic liquid for treatment of a tissue. The treatment can be therapeutic or prophylactic. The additive may be selected from the group consisting of tinctures, etchants, antiviral agents, antibacterial agents, pigment reducing agents, tallow dissolving agents and anti-inflammatory agents (such as acetyl salicylic acid). Preferably, dimethyl ether is used in combination with one or more additives. Because the device has been designed for an effective local administration of the cryogenic liquid with a minimal risk of contact between liquid and surrounding tissue and/or the environment, the risk of unwanted contact between additive with surrounding tissue and/or environment is likewise minimal.

The invention further provides a method for cold treating a tissue, in particular a wart, by means of a device or assembly according to the invention. The method comprises placing the device by the second opening thereof onto the tissue to be cooled, letting cryogenic liquid into the chamber, and keeping the device in position for a particular time. Such a method is reproducible because, given a same dosage, the tissue is cooled virtually independently of the ambient temperature. Moreover, the distance from the first opening to the tissue to be cooled is constant. Another advantage is that no actions need to be performed between the release of the cryogenic liquid and the application of the cold, these latter two actions being combined into one action with this method. Moreover, with this method no applicator needs to be connected with the spray can for taking up cryogenic liquid. In contrast with the prior art method utilizing an applicator, the present method allows much time for positioning the device relative to the tissue, since the intention is for the cryogenic liquid to be released at the moment when the device is properly positioned. While the device is being kept in position, no cold escapes that could cause unwanted damage. The device preferably comprises a first collar so that by placing the device by the second opening thereof onto the tissue to be cooled, the second opening is more easily closed off by the tissue. For initially freezing the tissue, the tissue is preferably first covered by the cryogenic liquid, after which the liquid evaporates. Keeping the device in position can be done for a period of 10 to 100 seconds, preferably between 10 and 40 seconds. Upon removal of the device, the tissue, owing to the evaporation of the residual cryogenic liquid, can eventually be cooled off additionally. The tissue being already cold by then, this extra low temperature will generally be experienced as less painful.

BRIEF DESCRIPTION OF THE DRAWINGS

The invention will be elucidated in the following on the basis of a non-limiting embodiment of a device according to the invention as shown by way of example only in the appended drawing, wherein.

DESCRIPTION OF PREFERRED EMBODIMENTS OF THE INVENTION

Figure 1:
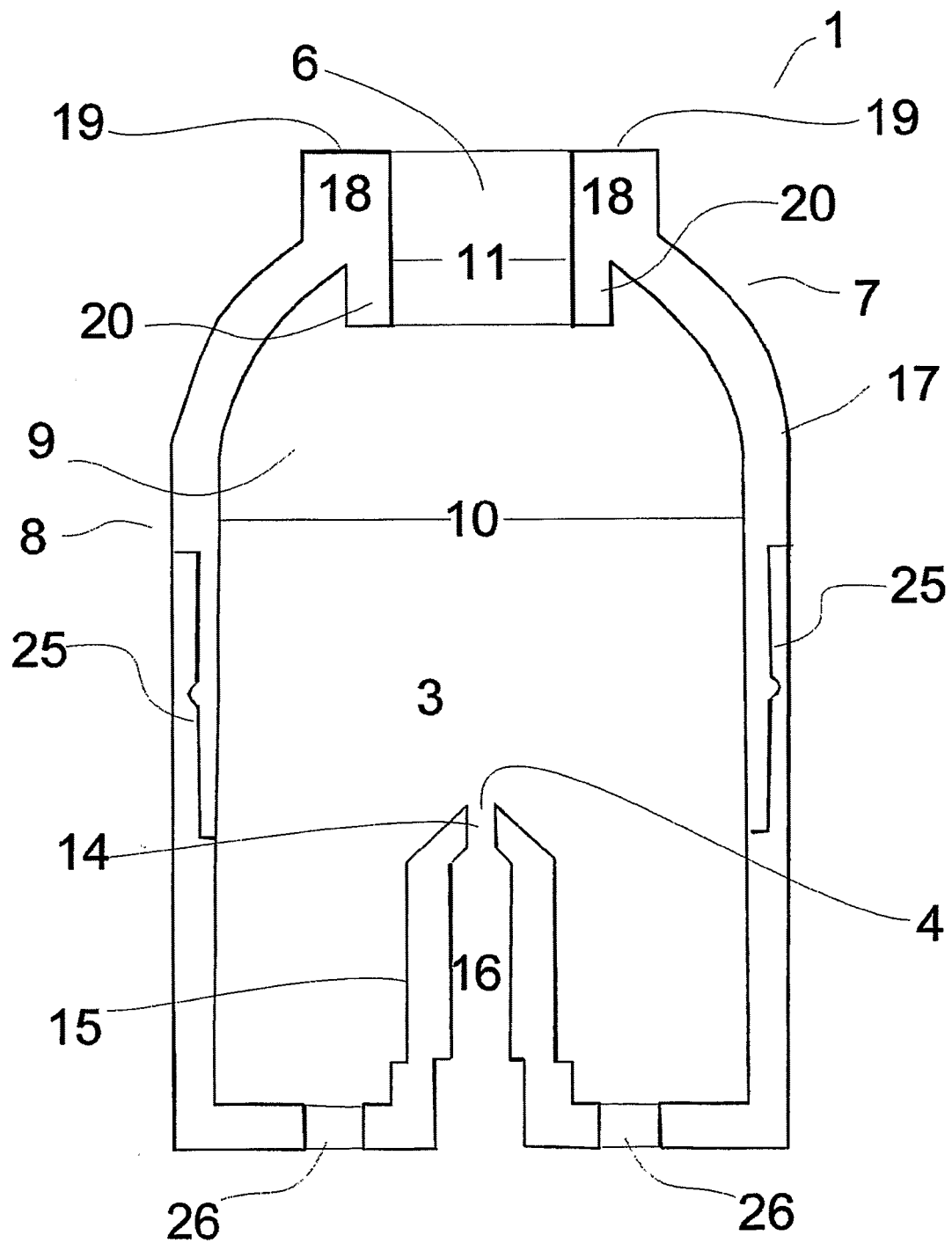
FIG. 1 is a cross section of a device according to the invention.

FIG. 1 shows a device (1) according to the invention, comprising a chamber (3) screened from the environment by a wall, which chamber (3) comprises a first opening (4) for letting cryogenic liquid (5) into the chamber (3). The volume and the elliptic paraboloid shape of the chamber (3) in this embodiment are such that evaporation of at least a part of the cryogenic liquid (5) is enabled and the cold generated through evaporation can be retained for some time and can be delivered to the tissue to be cooled (2). The chamber (3) further comprises a second opening (6) for delivering the cold to the tissue to be cooled (2), the second opening (6) being present in a first part (7), which first part (7) converges in the direction of the second opening (6), is semicircular and further is concentric with the second opening (6). The first opening (4) and the second opening (6) are herein coaxial. In this embodiment, a second part (8) of the chamber (3), which second part (8) adjoins the side (9) of the first part (7) facing away from the second opening (6), is cylindrical, the second part (8) and the second opening (6) are coaxial, and the first diameter (10) of the second part (8) is approximately 3 times greater than the second diameter (11) of the second opening (6). The first opening (4) in this embodiment is a passage (14) in a spray piece (15), which spray piece (15) comprises a channel (16) for allowing the cryogenic liquid (5) to pass out of the spray can (13), the channel (16) and the passage (14) being in line with each other and being directed towards the second opening (6). The device (1) comprises a first construction part (17), which first construction part (17) comprises the second opening (6) and is detachably connected with the remaining portion of the device (1). In this figure, it is indicated at 25 how the first construction part (17) is formed and can be slipped onto the remaining part of the device and be click-fitted. The chamber (3) comprises a cylinder-shaped first collar (18), directed towards the outside of the chamber (3), which first collar (18) surrounds the second opening (6). The end (19) of the first collar (18) facing away from the chamber (3) is wide and lies in one plane in this embodiment. The chamber (3) also comprises a second collar (20), directed towards the inside of the chamber (3), which second collar (20) surrounds the second opening (6). The chamber (3) further comprises third openings (vent holes) (26) to prevent overpressure in the chamber as a result of the spraying of the cryogenic liquid (5) into the chamber (3). These holes (26) are preferably not too large because otherwise too much cold might be lost as a result.

Figure 2:
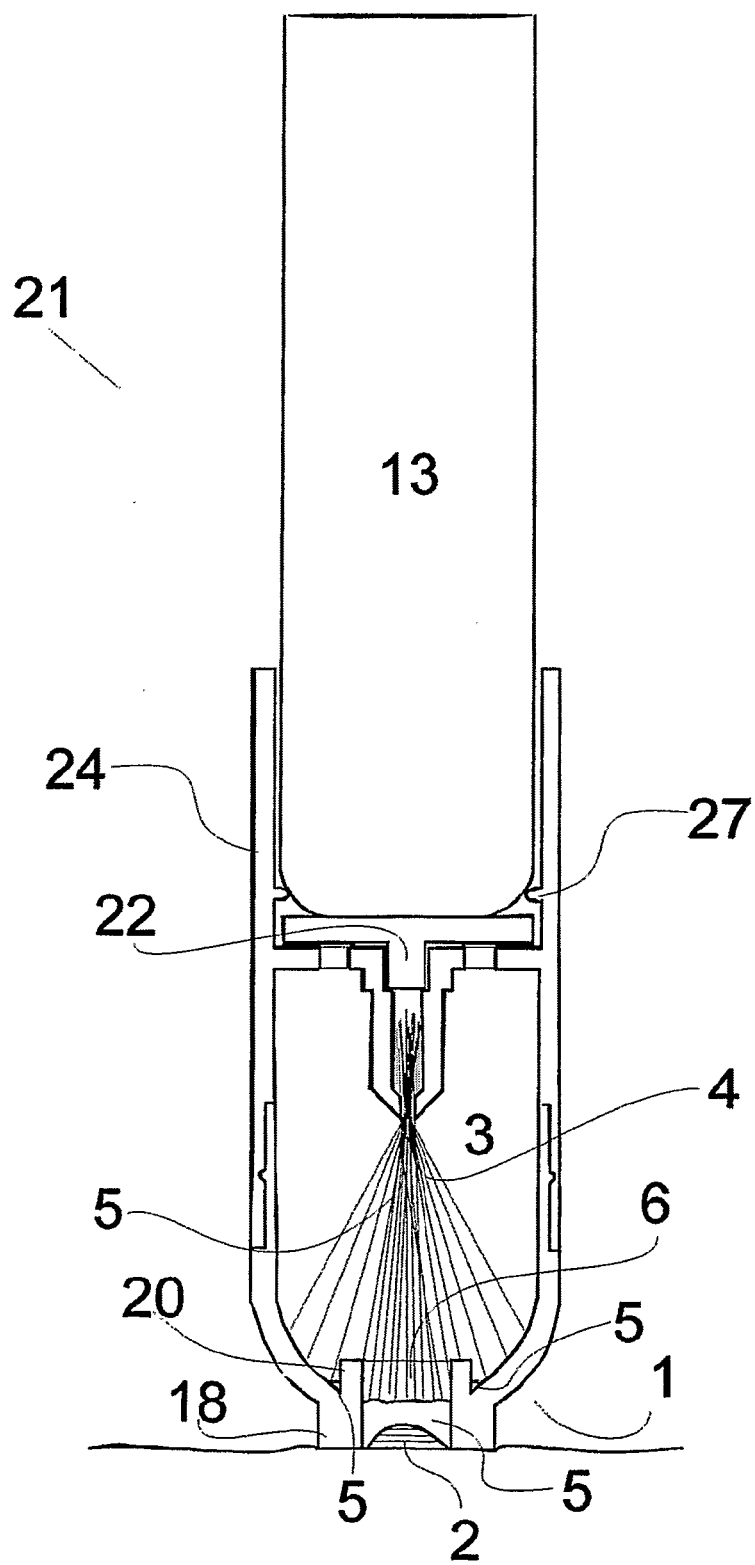
FIG. 2 is a cross section of an assembly according to the invention.

In the assembly (21) according to the invention shown in FIG. 2, the device (1) is a nozzle (1) of the spray can (13) and the flow and initial presence of the cryogenic liquid (5) are represented. By pressing the spray can (13) onto the nozzle (1), the dosing valve (22) of the spray can (13) is thereby activated, so that a dosed amount of the cryogenic liquid (5) leaves the spray can (13). It can be seen how the cryogenic liquid (5) comes out of the dosing valve (22) of the spray can (13) and, through the passage (14) and the channel (16), ends up mainly on the tissue to be cooled (2). Here, the tissue to be cooled (2) is a protrusion, such as a wart. Initially, the tissue to be cooled (2) can be covered with cryogenic liquid (5), which is held in the first collar (18) and will then evaporate. It can also be seen that cryogenic liquid (5) that impacts the wall of the chamber (3) ends up in a little gutter which is formed inter alia by the second collar (20). It can be seen that the first collar (18) isolates the tissue to be cooled (2) from the other part of the skin and that the cold treatment involves only the tissue to be cooled (2). Even though the nozzle (1) is pressed with some force around the tissue to be cooled (2), the discomfort around the tissue to be cooled (2) will not be great owing to the wide end (19) of the first collar (18) facing away from the chamber (3). The device (1) in this embodiment is connected with the spray can (13) by means of a jacket (24) connected with the device (1). This jacket (24) is situated around the spray can (13) and comprises protrusions which keep the spray can in the jacket. Between the spray can (13) and the jacket (24) there is some freedom of movement which is defined inter alia by protrusions (27) of the jacket (24). This freedom of movement is necessary for activating the dosing valve by pressing the spray can in the direction of the device and for moving the spray can in the reverse direction again, possibly for activating the dosing valve (22) once more. This embodiment is implemented such that the jacket (24) has the same outside diameter as the device and also encloses the spray can (13).

Example 1

To illustrate the safe and efficient cooling of a tissue utilizing a device according to the invention, temperature measurements were performed inside a chamber, on the wall of the chamber, and on the tissue. The test material was a piece of pigskin of a thickness of circa 2 mm, to which a punched-out piece of pigskin of a diameter of approximately 5 mm had been applied. The punched-out piece of pigskin can be regarded as a wart. First, an assembly with a device according to the invention was placed, by way of the second opening, over the "wart". Next, dimethyl ether was introduced into the chamber of paraboloid shape by actuating the dosing valve of a spray can with cryogenic liquid three times (see arrow in FIG. 3). After that, the assembly was held in the same place for approximately 50 seconds.

Figure 3:
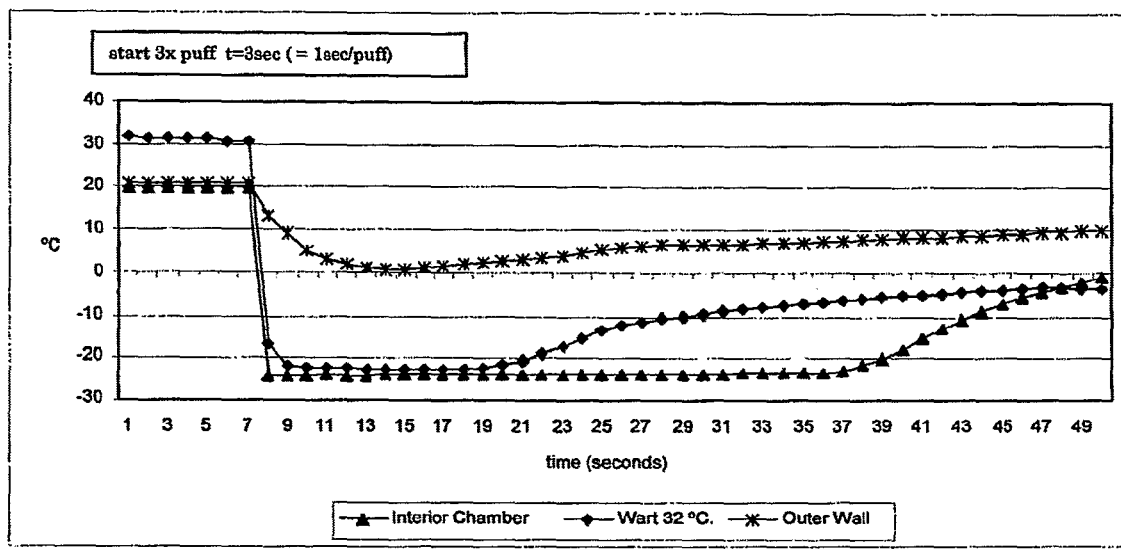
FIG. 3 shows the temperature (° C.) of the interior of the chamber, the wall of the chamber and of a wart, as a function of time (seconds) after a cold treatment with an application cap according to the invention. The ambient temperature was 20° C. and the initial temperature of the wart is 32° C. (see Example 1). The arrow indicates the moment at which the cryogenic liquid was introduced into the chamber.

FIG. 3 shows both the insulating effect and the evaporation/cold effect. The treated tissue was cooled for at least 10 seconds to a temperature lower than −20° C., while the outer wall of the device did not fall below the freezing-point.

Example 2

This example shows the protection of the surroundings of the tissue to be treated (e.g. wart) before, during and after treatment. As in Example 1, pigskin was used as test material. Two overdosage tests were performed by applying excessive cryogenic liquid onto the tissue, that is, 5× or 10× instead of 3× actuation of the dosing valve.

Test 1:

10× puffing and then waiting for 10 seconds before the application cap is taken off the skin.

Results:

After removal of the application cap, the cryogenic liquid that was still present in the chamber of the application cap flows over the skin.

Figure 4:
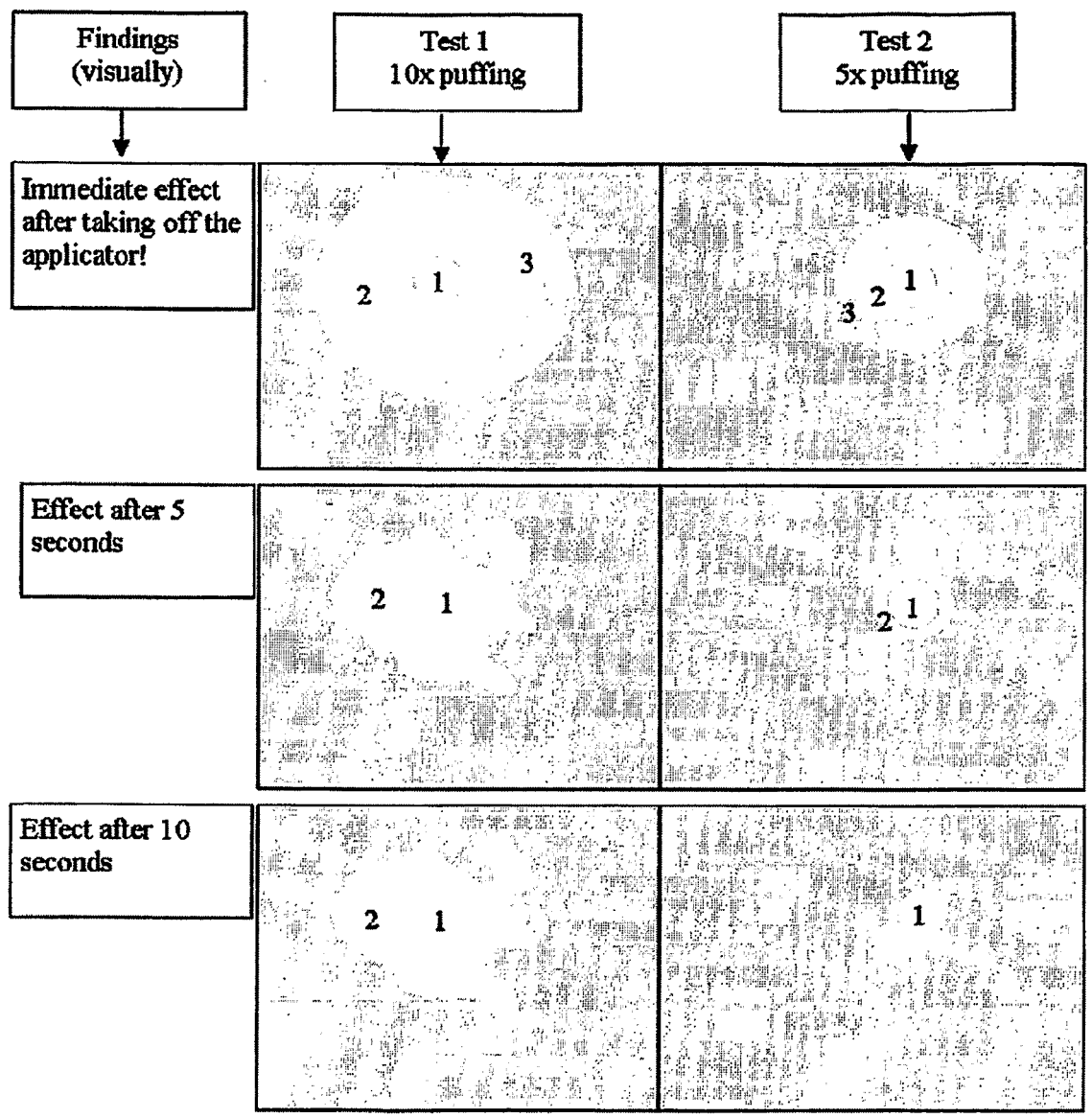
FIG. 4 shows a graphic representation of the visual observations of a pigskin which has been treated with an overdosage of a cryogenic liquid by means of an assembly according to the invention, as described in Example 2. Panels A show the situations directly upon removal of the application cap, and Panels B and C show the effect after 5 and 10 seconds, respectively, after removal of the application cap. The areas indicated with the numerals 1, 2, and 3 represent the relative extent of cooling of the skin, with area 1 being frozen most and area 3 being frozen least.

Visually (see FIG. 4):

The small circle (1) is frozen most and also remains coldest longest.

The larger circle (2) is partially frozen by the large amount of liquid that is still in the cap at the moment when the application cap is removed. The cryogenic liquid evaporates and flows away over the skin. A portion freezes a little but regains color soon (3).

Test 2:

5× puffing and then waiting for 10 seconds before the application cap is taken off the skin.

Results:

The liquid remains in the application cap during puffing. No leakage occurs.

Visually (see FIG. 4):

A small white circle appears at the point where the nozzle had been placed (1).

The second ring also freezes to some extent, but regains color soon. (2)

On the surface within the delineated outer ring comes liquid, but it does not become white through freezing (3).

The invention claimed is:

1. A device for use together with a container containing a cryogenic liquid for cold treating a tissue, which device comprises a chamber screened from the environment by a wall, which chamber comprises:
   a first opening formed by a passage in a spray piece, the spray piece extending from the wall into the chamber and having a channel therethrough, wherein the channel and the passage are adapted for being in communication with an outlet opening of the container for letting the cryogenic liquid into the chamber,
   a second opening for delivering the cold to the tissue to be cooled,
   a first part of the chamber, in which the second opening is present, comprises an essentially semispherical portion and a circumferential side wall, wherein the circumferential side wall is essentially concentric with the second opening and the essentially semispherical portion converges in the direction of the second opening,
   a second part of the chamber, in which the first opening is present, that is essentially cylindrical, wherein the second part has a first diameter and adjoins the circumferential side wall of the first part facing away from the second opening, and
   at least one third opening in the wall facing away from the second opening and adjacent the channel, wherein the at least one third opening prevents excess pressure upon spraying of cryogenic liquid into the chamber.

2. An assembly of a device for cold treating a tissue according to claim 1, and a container with cryogenic liquid, and wherein the outlet opening of the container is in communication with the first opening.

3. An assembly according to claim 2, wherein the container is a spray can with cryogenic liquid, and wherein the outlet opening is a valve which is in communication with the first opening.

4. An assembly according to claim 3, wherein the valve is a dosing valve.

5. An assembly according to claim 2, wherein the container contains a halogen-free cryogenic liquid, for instance dimethyl ether or liquid nitrogen, optionally comprising at least one additive which can be used in a directed manner and/or in cooperation with the cryogenic liquid.

6. An assembly according to claim 5, wherein the additive is chosen from the group consisting of tinctures, etchants, antiviral agents, antibacterial agents, pigment reducing agents, tallow dissolving agents and anti-inflammatory agents.

7. An assembly according to claim 2, wherein the container contains an amount of cryogenic liquid which has been adjusted for 2-4 cold treatments.

8. An assembly according to claim 2, wherein the container contains an amount of cryogenic liquid which is sufficient for at least 100 cold treatments.

9. A method for cold treating a tissue, in particular a wart, by means of an assembly according to claim 2, which method comprises:
   placing the assembly by the second opening of device onto the tissue to be cooled,
   letting cryogenic liquid from container into the chamber, and
   keeping the assembly in position for a particular time.

10. A device according to claim 1, wherein the chamber comprises a first cylindrical collar, directed towards the outside of the chamber, which first collar surrounds the second opening.

11. A device according to claim 10, wherein the first collar is detachably connected with the device.

12. A device according to claim 10, wherein the end of the first collar facing away from the chamber is 1-5 millimeters wide and lies in one plane.

13. A device according to claim 10, wherein the end of the first collar facing away from the chamber is 2-3 millimeters wide and lies in one plane.

14. A device according to claim 1, wherein the first opening and the second opening are essentially coaxial.

15. A device according to claim 1, wherein the first part of the chamber is essentially semicircular and is essentially concentric with the second opening.

16. A device according to claim 1, wherein the first part of the chamber has essentially the shape of an elliptic paraboloid.

17. A device according to claim 1, wherein
   the second opening has a second diameter and wherein the second part and the second opening are essentially coaxial, and the first diameter of the second part is 2 to 5 times greater than the second diameter of the second opening.

18. A device according to claim 1, wherein the volume of the chamber is at least 1 cm$^3$.

19. A device according to claim 1, wherein the chamber comprises two third openings to prevent excess pressure upon spraying of cryogenic liquid into the chamber.

20. A device according to claim 1, wherein the channel and the passage are in line with each other and are directed towards the second opening.

21. A device according to claim 1, wherein it comprises a first construction part, which first construction part comprises the second opening and is detachably connected with the remaining portion of the device.

22. A device according to claim 1, wherein the chamber comprises a second collar, directed towards the inside of the chamber, which second collar surrounds the second opening.

23. A device according to claim 1, wherein at least a part of the wall of the chamber is provided with a temperature indicator.

24. A device according to claim 1, wherein the volume of the chamber is between 1 and 20 cm$^3$.

25. A kit of parts for a device for cold treating a tissue, the kit comprising:
- a container having an outlet opening and containing a cryogenic liquid; and
- a chamber screened from the environment by a wall, wherein the chamber comprises:
  - a first opening formed by a passage in a spray piece, the spray piece extending from the wall into the chamber and having a channel therethrough, wherein the channel and the passage are adapted for being in communication with an outlet opening of the container for letting the cryogenic liquid into the chamber,
  - a second opening for delivering the cold to the tissue to be cooled,
  - a first part of the chamber, in which the second opening is present, comprises an essentially semispherical portion and a circumferential side wall, wherein the circumferential side wall is essentially concentric with the second opening and the essentially semispherical portion converges in the direction of the second opening,
  - a second part of the chamber, in which the first opening is present, that is essentially cylindrical, wherein the second part has a first diameter and adjoins the circumferential side wall of the first part facing away from the second opening, and
- at least one third opening in the wall facing away from the second opening and adjacent the channel, wherein the at least one third opening prevents excess pressure upon spraying of cryogenic liquid into the chamber.

* * * * *

UNITED STATES PATENT AND TRADEMARK OFFICE
CERTIFICATE OF CORRECTION

PATENT NO.        : 8,562,597 B2
APPLICATION NO.   : 12/301628
DATED             : October 22, 2013
INVENTOR(S)       : Van Der Heijden et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1087 days.

Signed and Sealed this
Fifteenth Day of September, 2015

Michelle K. Lee
*Director of the United States Patent and Trademark Office*